US008974586B2

(12) United States Patent
Richard et al.

(10) Patent No.: US 8,974,586 B2
(45) Date of Patent: Mar. 10, 2015

(54) DENTAL COMPOSITION

(75) Inventors: Gilles Richard, Crosne (FR); Olivier Marie, Soisy sur Seine (FR)

(73) Assignee: Septodont ou Septodont SAS ou Specialties Septodont, Sainr Maur des Fosses (FR)

( * ) Notice: Subject to any disclaimer, the term of this patent is extended or adjusted under 35 U.S.C. 154(b) by 99 days.

(21) Appl. No.: 13/639,688

(22) PCT Filed: Apr. 5, 2011

(86) PCT No.: PCT/FR2011/050764
§ 371 (c)(1),
(2), (4) Date: Oct. 5, 2012

(87) PCT Pub. No.: WO2011/124841
PCT Pub. Date: Oct. 13, 2011

(65) Prior Publication Data
US 2013/0025498 A1 Jan. 31, 2013

(30) Foreign Application Priority Data

Apr. 7, 2010 (FR) ..................................... 10 52631

(51) Int. Cl.
| A61K 6/06 | (2006.01) |
| A61K 6/00 | (2006.01) |
| A61L 24/02 | (2006.01) |
| A61L 26/00 | (2006.01) |
| A61K 6/02 | (2006.01) |

(52) U.S. Cl.
CPC .............. *A61K 6/0008* (2013.01); *A61K 6/0606* (2013.01); *A61L 24/02* (2013.01); *A61K 6/0038* (2013.01); *A61L 26/0004* (2013.01); *A61K 6/0094* (2013.01); *A61K 6/024* (2013.01); *A61K 6/0612* (2013.01); *A61K 6/0668* (2013.01); *A61K 6/0675* (2013.01)
USPC .............. 106/35; 106/712; 106/733; 106/728; 106/738; 433/224; 433/228.1; 433/218

(58) Field of Classification Search
CPC .. A61L 24/02; A61L 26/0004; A61K 6/0038; A61K 6/0094; A61K 6/0606; A61K 6/0612
USPC ......... 433/224, 228.1, 218; 106/35, 712, 733, 106/728, 738
See application file for complete search history.

(56) References Cited

U.S. PATENT DOCUMENTS

| 2,122,011 | A | 6/1938 | Schoenbeck et al. ............ 106/35 |
| 2,901,377 | A | 8/1959 | Bode et al. .................... 428/413 |
| 4,381,918 | A | 5/1983 | Ehrnford et al. ............... 523/115 |
| 4,647,600 | A | 3/1987 | Kawara et al. ................. 523/116 |
| 5,415,547 | A | 5/1995 | Torabinejad et al. ...... 433/228.1 |
| 5,584,926 | A | 12/1996 | Borgholm et al. ............. 106/713 |
| 6,334,775 | B2 | 1/2002 | Xu et al. ..................... 433/228.1 |
| 6,652,282 | B2 | 11/2003 | Jensen et al. ................ 433/228.1 |
| 6,858,074 | B2 | 2/2005 | Anderson et al. ............. 106/724 |
| 7,819,663 | B2 * | 10/2010 | Bergaya et al. ................ 433/226 |
| 7,942,961 | B2 | 5/2011 | Asgary ............................ 106/35 |
| 2002/0045678 | A1 | 4/2002 | Lopez et al. ................... 523/116 |
| 2002/0198283 | A1 | 12/2002 | Imai et al. ...................... 523/116 |
| 2003/0127026 | A1 | 7/2003 | Anderson et al. ............. 106/724 |
| 2005/0025622 | A1 | 2/2005 | Djeridane et al. .......... 416/97 R |
| 2006/0102049 | A1 | 5/2006 | Bergaya et al. ................. 106/35 |
| 2007/0009858 | A1 | 1/2007 | Hatton et al. .................. 433/224 |
| 2007/0072957 | A1 | 3/2007 | Noguchi et al. ............... 523/116 |
| 2008/0085948 | A1 | 4/2008 | Primus et al. .................. 523/116 |
| 2011/0281241 | A1 | 11/2011 | Pandolfelli et al. ........... 433/224 |
| 2012/0270184 | A1 | 10/2012 | Richard et al. ................ 433/224 |

FOREIGN PATENT DOCUMENTS

| DE | 1 992 3956 | 11/2000 |
| FR | 2 603 274 | 3/1988 |
| JP | 03-165773 | 7/1991 |
| JP | 2003-286176 | 10/2003 |
| RU | 2 197 940 | 2/2003 |
| WO | 93/21122 | 10/1993 |
| WO | 01/76534 | 10/2001 |
| WO | 2004/017929 | 3/2004 |
| WO | 2005/087178 | 9/2005 |
| WO | 2008/000917 | 1/2008 |
| WO | 2008/100451 | 8/2008 |
| WO | 2008/102214 | 8/2008 |
| WO | 2013/041709 | 3/2013 |

OTHER PUBLICATIONS

D. P. Bentz et al., "Effects of cement particle size distribution on performance properties of portland cement based materials", Cement and Concrete Research, vol. 29, N° 10, Oct. 1999, pp. 1663-1671.
International Research Report, dated Dec. 17, 2012, from the patent application WO2013/041709.
Abstract of published Japanses Translation No. 2009-512713 of the PCT International Application.
Abstract of published Japanese Translation No. 2010-518093 of the PCT International Application.

* cited by examiner

*Primary Examiner* — Carol M Koslow
(74) *Attorney, Agent, or Firm* — Norton Rose Fulbright US LLP

(57) ABSTRACT

One subject of the invention is a composition comprising from 5 to 65%, by weight relative to the total weight of the composition, of calcium silicate crystals; from 1 to 20%, by weight relative to the total weight of the composition, of calcium carbonate crystals; in addition from 0 to 50%, preferably from 1 to 40%, by weight relative to the total weight of the composition, of a compound of general formula $mCaO \cdot nSiO_2 \cdot pH_2O$ in which m and n, each independently, vary from 1 to 3 and p varies from 3 to 6; the ratio between the particle size d50 of the calcium silicate crystals and the particle size d50 of the calcium carbonate crystals being less than 10; another subject of the invention is a process for preparing said composition, and also the use of said composition in the dental field.

18 Claims, No Drawings

DENTAL COMPOSITION

This application is a national phase application under 35 U.S.C. § 371 of International Application No. PCT/FR2011/050764 filed 5 Apr. 2011, which claims priority to French Application No. 1052631 filed 7 Apr. 2010. The entire contents of each of the above-referenced disclosures is specifically incorporated herein by reference without disclaimer.

The present invention relates to a novel composition for restoring mineralised substance, in particular in the dental field. More specifically, the composition of the invention is useful for restoring dental crowns that have suffered a loss of substance, for endodontic treatment, and in dental surgery.

Restoration, within the present invention, refers to the reconstitution of damaged teeth following an impact or a bacterial or viral infection, in particular decay, especially the filling of cavities.

In dental practice, silver amalgam was used for a long time for restoring dental crowns and was particularly appreciated since it afforded an average filling duration of 14 years. However, its formulation comprised mercury, which was susceptible to be released in the saliva, and to become a threat for the health of the patient. Moreover, its metallic appearance was unaesthetic.

The composite resins that were next proposed as an alternative to silver amalgam solved the aesthetic problem but afforded effective filling only for approximately 7 years.

The ionomer glass cements that were also developed proposed an aesthetically possible solution but had drawbacks that generally limited their use to the filling of temporary teeth: in particular, it is impossible to place them in direct contact with the pulp tissues and their mechanical strength is limited.

Obtaining improved mechanical properties, in particular good mechanical resistance to compression, an extended life and excellent biocompatibility is a veritable challenge in the field of dental compositions. Indeed, the dental compositions of the prior art, which use cements of the Portland type, have good biological properties but relatively mediocre mechanical properties. The applicant analysed the composition of Portland cements and identified that the presence of aluminate impaired the mechanical properties of the final composition. One technical problem to be solved was therefore being capable of producing a dental composition not containing aluminate.

Composition of Portland cement

| | Chemical formula | Usual name | Quantity by weight in Portland cement (% w/w) |
|---|---|---|---|
| Tricalcium silicate | $Ca_3SiO_5$ | C3S | 40-65 |
| Dicalcium silicate | $Ca_2SiO_4$ | C2S | 10-20 |
| Tricalcium aluminate | $Ca_3Al_2O_6$ | C3A | 10 |
| Tetracalcium aluminoferrite | $Ca_4Al_2Fe_2O_{10}$ | C4AF | 10 |
| Calcium sulfate dihydrate | $CaSO_5 \cdot 2H_2O$ | CSH2 | 2-5 |

The composition that is the subject of patent EP 1 531 779, filed in 2003 by the applicant, proposes a preparation for producing a restoration material that enables to obtain a material having both acceptable aesthetic appearance and acceptable resistance to compression, of around 100 to 200 MPa.

However, there still exists a demand on the part of patients and practitioners for dental compositions having good mechanical properties, and the present invention is an alternative to the compositions that are the subject matter of patent EP 1 531 779.

In the context of researches that the applicant is carrying out in order to constantly optimise the dental compositions that it markets, the applicant realised, contrary to the prejudice of persons skilled in the art, that the compositions having the best mechanical properties were not those made from stacks of coarse calcium silicate crystals in which small calcium carbonate crystals were inserted, but those made of calcium silicate crystals having the same order of magnitude in size as calcium carbonate crystals. Using calcium carbonate crystals having a d50 granulometry of around 2 to 4 microns also enabled to avoid phenomena of demixing of the composition, leading to numerous industrial rejects.

Starting from this finding, the applicant then succeeded in completely mastering the method of manufacturing the compositions according to the invention and in particular the process of forming the compound used as a join between the various crystals in the final composition.

This compound, having the function of a join between the various crystals present in the final composition, is a product of the reaction of calcium silicate with water. It is generally referred to as CSH. For example, in the case of tricalcium silicate:

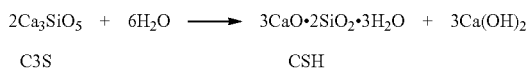

C3S         CSH

CSH is a product of general formula $mCaO \cdot nSiO_2 \cdot pH_2O$ in which n and m, each independently, vary from 1 to 3, and p varies from 3 to 6. In the embodiment of tricalcium silicate, m is 3, n is 2 and p is 3. CSH is a hydrate that forms by heterogeneous germination on the surface of the tricalcium silicate crystals and develops by aggregation of nanocrystals in order to cover the entire surface of the calcium silicate crystals. It is this aggregation which, by increasing the contacts between the crystals, is at the origin of the increase over time of the mechanical strength of the composition of the invention.

Thus the invention relates to a composition in which the nature and granulometry of the solids is perfectly controlled and the quantity of CSH formed is also controlled.

More precisely, the present invention relates to a dental composition comprising:

from 5% to 65%, preferably 8% to 60%, more preferentially 10% to 35% by weight with respect to the total weight of the composition, of calcium silicate, said calcium silicate preferably being chosen from the group comprising tricalcium silicate and/or a mixture of dicalcium silicate and tricalcium silicate, from 1% to 20%, preferably 2% to 15% by weight with respect to the total weight of the composition, of calcium carbonate, and from more than 0% to 50%, preferably 1% to 40% by weight with respect to the total weight of the composition, of $mCaO \cdot nSiO_2 \cdot pH_2O$ (CSH) in which m and n, each independently, vary from 1 to 3 and p varies from 3 to 6; advantageously, said percentage of CSH is from more than 0% to less than 3.5% by weight with respect to the total weight of the composition for 1 to 6 minutes as from the formation of said composition, this period being referred to as the working time; advantageously, said percentage of CSH is from 3.5% to 8%, preferably 4% to 6% by weight with respect to the total weight of the composition for 6 to 15 minutes as from the formation of the composition, this period being referred to as the setting time;

the ratio between the d50 granulometry of the calcium silicate crystals and the d50 granulometry of the calcium carbonate crystals is less than 10; preferably this ratio is 0.1 to 9, very preferentially 0.2 to 5, even more preferentially 0.5 to 2.

According to the invention, the granulometry is measured by a Beckman-Coulter LS230 granulometer appliance with SVM module. The value "d10" means that 10% of the crystals of the compound in question have a diameter of less than said value. The value "d50" means that 50% of the crystals of the compound in question have a diameter of less than said value. The value "d90" means that 90% of the crystals of the compound in question have a diameter of less than said value. The value "d99.9" means that 99.9% of the crystals of the compound in question have a diameter of less than said value.

Advantageously the d50 of calcium silicate is 1 to 5.5 microns, preferably 3 to 4 microns. Advantageously the d50 of calcium carbonate is 1 to 5.5 microns, preferable 2 to 4 microns. According to one embodiment of the invention, the composition according to the invention is such that the ratio between the d50 granulometry of the calcium silicate crystals and the d50 granulometry of the calcium carbonate crystals is less than 10; preferably this ratio is from 0.1 to 9, very preferentially from 0.2 to 5, even more preferentially from 0.5 to 2.

Advantageously the d10 of calcium silicate is 0.2 to 1 micron, preferably 0.7 to 0.8 micron. Advantageously the d10 of calcium carbonate is 0.2 to 1 micron, preferable 0.6 to 0.8 microns. According to one embodiment of the invention, the composition according to the invention is such that the ratio between the d10 granulometry of the calcium silicate crystals and the d10 granulometry of the calcium carbonate crystals is less than 10; preferably this ratio is from 0.1 to 9, very preferentially from 0.2 to 4, even more preferentially from 0.5 to 2.

Advantageously the d90 of calcium silicate is 6 to 20 microns, preferably 7 to 14 microns. Advantageously the d90 of calcium carbonate is 6 to 20 microns, preferable 9 to 14 microns. According to one embodiment of the invention, the composition according to the invention is such that the ratio between the d90 granulometry of the calcium silicate crystals and the d90 granulometry of the calcium carbonate crystals is less than 10; preferably this ratio is from 0.1 to 9, very preferentially from 0.2 to 5, even more preferentially from 0.5 to 4.

Advantageously the d99.9 of calcium silicate is 9 to 25 microns, preferably 10 to 15 microns. Advantageously the d99.9 of calcium carbonate is 15 to 25 microns, preferable 22 to 24 microns. According to one embodiment of the invention, the composition according to the invention is such that the ratio between the d99.9 granulometry of the calcium silicate crystals and the d99.9 granulometry of the calcium carbonate crystals is less than 10; preferably this ratio is from 0.1 to 9, very preferentially from 0.2 to 5, even more preferentially from 0.5 to 4.

According to a first embodiment, the calcium silicate is pure tricalcium silicate.

In another embodiment, the calcium silicate is a mixture comprising or essentially comprising tricalcium silicate and dicalcium silicate. Advantageously, this mixture is such that it comprises no more than 10% by weight of dicalcium silicate with respect to the total weight of the calcium silicates present in the composition, typically dicalcium silicate and tricalcium silicate. According to a preferred embodiment, the mixture comprises or consists of 0% to 10% dicalcium silicate and 90% to 100% tricalcium silicate, by weight with respect to the total weight of the calcium silicates. The term "consists of" means in particular that the mixture does not contain any calcium silicate other than dicalcium silicate and tricalcium silicate.

According to a preferred embodiment, the mixture does not contain any aluminate. According to another preferred embodiment, the mixture does not contain any calcium sulphate.

According to the invention the setting kinetics is a mathematical function, preferably a linear regression, of the compressive strength of the composition according to the invention. According to a preferred embodiment, the percentage of CSH present in the composition of the invention can be measured by linear regression of the compressive strength of the composition. Thus a composition according to the invention that was manufactured approximately 15 minutes ago has a compressive strength of approximately 43.5 MPa, corresponding to approximately 5% by weight of CSH in the composition.

Advantageously, the composition comprises a setting accelerator, preferably calcium oxide. Calcium oxide may be present in a quantity varying from 0% to 3%, preferably 0.1% to 1% by weight with respect to the total weight of the composition. The function of calcium oxide is to accelerate the hydration of the calcium silicate crystals and therefore the formation of CSH and setting.

According to a preferred embodiment, the composition according to the invention comprises at least one radio-opacifier, preferably zirconium oxide and bismuth oxide. Radio-opacifiers increase the radio-opacity of the composition according to the invention, thus enabling radiographic checking of the restoration carried out by the practitioner. Advantageously, the quantity of radio-opacifier, preferably zirconium oxide, in the composition according to the invention is 2% to 25%, preferably 5% to 20% by weight with respect to the total weight of the composition. According to a preferred embodiment, the radio-opacifier used, preferably zirconium oxide, has a granulometry of the same order of magnitude as the calcium carbonate and calcium silicate. Advantageously, the d10 of zirconium oxide is 0.1 to 0.4 micron, preferably approximately 0.2 micron. Advantageously, the d50 of zirconium oxide is 1 to 4 microns, preferably 2 to 3 microns. Advantageously the d90 of zirconium oxide is 6 to 8 microns, preferably approximately 7 microns. According to a preferred embodiment, the ratio between the d50 granulometry of calcium silicate and the d50 granulometry of radio-opacifier is less than 10; preferably this ratio is 0.1 to 9, very preferentially 0.2 to 5, even more preferentially 0.5 to 4.

Within the meaning of the present invention, the term "approximately" followed by numerical data signifies the numerical data plus or minus 10% of the numerical data.

Advantageously, the composition also comprises a plasticiser, for example polyfunctional monomers of methacrylate and acrylate types (e.g., Neomer ™ products by Sanyo Chemicals) or modified polycarboxylate ethers (e.g., Glenium® product by BASF Corporation). Advantageously, the composition according to the invention comprises 0.1% to 1% by weight of plasticiser, with respect to the total weight of the composition.

Advantageously, the composition according to the invention also comprises pigments, preferably iron oxides. Advantageously, said iron oxides are chosen from yellow, red and brown iron oxides. Advantageously, the composition comprises less than 1.5%, preferably 0.5% to 1% by weight of pigments with respect to the total weight of the composition. In various embodiments, the composition is at least one iron oxide.

Advantageously, the elastic modulus of the composition according to the invention, in the period of time ranging from 1 to 6 minutes as from the end of the mixing, is less than 20 MPa, preferably less than 10 MPa, and in the period from 11 to 20 minutes exceeds 100 MPa. The elastic modulus is useful for measuring the working time of the composition of the invention, which corresponds to the time between the end of mixing and the start of setting, and which is 1 to 6 minutes, preferably approximately 6 minutes, and for measuring the setting time, which is 6 to 15 minutes, preferably approximately 10 minutes.

The elastic modulus is measured by a controlled-deformation rheometer of the ARES type sold by Rheometric Scientific Inc, Piscataway, N.J., USA, under the conditions described hereafter: after mixing, the composition is placed between two serrated parallel planes 6 mm in diameter, the air gap of which is 2 mm. Only the bottom plane is at the controlled temperature of 37° C., a closed chamber keeping all the sample at temperature and at 100% relative humidity in order to prevent drying thereof. The experimental conditions are as follows: frequencies of the oscillations at one radian per second, deformation applied: 0.0005%. Under these conditions, the deformation is less than the critical deformation beyond which any cement paste disintegrates (around 0.0015%) and the force transmitted is proportional to the deformation. It is thus possible to measure the change in the elastic modulus G' of the material as a function of time, without any modification to the structure of the material.

Preferably, the compressive strength of the composition of the invention at one hour is greater than 50 MPa and reaches around 200 MPa after a few days, typically 7 days, in order to reach 300 MPa at one month. Accordingly, the compressive strength of said composition is greater than 50 MPa when the composition was manufactured more than one hour ago or more than 24 hours ago.

According to one embodiment, the compressive strength of the composition of the invention at 24 hours is greater than 50 MPa. According to another embodiment, the compressive strength of the composition of the invention at 24 hours is greater than 100 MPa. According to another embodiment, the compressive strength of the composition of the invention at 24 hours is greater than 150 MPa.

The compressive strength is measured with reference to ISO 9917-1: 2007. The test tubes are prepared after mixing, using cylindrical Teflon moulds 4 mm in diameter and 6 mm high. In filling the moulds care is taken to eliminate the air bubbles from the paste, stored in an incubator for 15 minutes at 37° C. and 100% relative humidity for the required setting time. The test tubes are then removed from the mould and stored under distilled water at 37° C. for the wanted setting time. The samples are thus preserved under conditions close to their future conditions of clinical use. The compressive strength of the test tubes is measured on four occasions, i.e. 1 hour, 1 day, 7 days and 28 days, by means of a Universal press (model 2/M, MTS Systems, 1400 Eden Prairie, Minneapolis, USA) with a speed of movement of 0.5 mm per minute.

Advantageously, the porosity of the composition according the invention is less than 10%, preferably between 2% and 8%, preferentially approximately 7%. The porosity of the composition of the invention was measured by mercury intrusion porosimetry (MIP) using a Micromeritics Autopore III instrument in a pressure range varying from 0.001 to 414 MPa, which enables to access pores with an entry diameter comprised between 3 nm and 360 microns. Alternatively, the mobility of the ions, which indicates the number of pores and the size of the pores, is measured by electrical resistance: after the initial setting, the material continues to improve in terms of internal structure, in order to become more and more dense and less and less porous.

The invention also relates to a method for preparing the composition according to the invention, in which a mixture of a solid phase and an aqueous phase is produced, for example by means of a conventional vibrating mixer, at 4200 oscillations per minute for 10 to 50 seconds, typically 30 seconds.

The solid phase comprises tricalcium silicate or a mixture of tricalcium silicate and dicalcium silicate. According to a first embodiment, the solid phase comprises calcium silicates chosen from tricalcium silicate and a mixture of tricalcium silicate $Ca_3SiO_5$ and dicalcium silicate $Ca_2SiO_4$. Advantageously, said mixture of tricalcium silicate and dicalcium silicate comprises no more than 10% by weight of dicalcium silicate with respect to the total weight of the calcium silicates present in the composition, typically dicalcium silicate and tricalcium silicate. Advantageously, the tricalcium silicate used in the composition of the invention is such that its free lime content is less than 2.0% by weight with respect to the weight of tricalcium silicate. According to a preferred embodiment, the calcium to silica mol ratio in the tricalcium silicate of the invention is 2.95 to 3.05. The tricalcium silicate, or mixture of tricalcium silicate and dicalcium silicate, used in the initial composition intended to become the composition of the invention is in the form of a fine, white or roughly white, hygroscopic powder.

The solid phase also comprises calcium carbonate $CaCO_3$, which is in the form of a white or roughly white powder practically insoluble in water.

According to a first preferred embodiment, the solid phase also comprises a radio-opacifier of the type in particular of zirconium oxide $ZrO_2$ or bismuth, which is in the form of a white powder practically insoluble in water.

According to a second preferred embodiment, the solid phase also comprises calcium oxide CaO, which is in the form of a granular powder, white or slightly yellowish to greyish in dilute acids and practically insoluble in ethanol.

Advantageously, the solid phase comprises pigments, in particular iron oxides. Preferably, the solid phase comprises yellow iron oxide Fe(O)OH, containing at a minimum 60% iron by weight with respect to the total weight of this pigment, which is in the form of a yellow powder practically insoluble in water and alcohol; red iron oxide Fe(O)OH, containing at a minimum 60% iron by weight with respect to the total weight of this pigment, which is in the form of a red powder practically insoluble in water and in alcohol; brown iron oxide, which is a mixture of three iron oxides: red iron oxide: $Fe_2O_3$, yellow iron oxide: $Fe_2O_3$, $H_2O$, black iron oxide: $Fe_3O_4$; brown iron oxide contains more than 60% iron by weight with respect to the total weight of this pigment and is in the form of: a brown, magnetic and electrostatic powder, practically insoluble in water and in 96% ethanol.

According to a preferred embodiment, the solid phase comprises:
  a mixture of tricalcium silicate and dicalcium silicate comprising more than 90% by weight of tricalcium silicate and less than 10% by weight of dicalcium silicate, with respect to the total weight of the calcium silicates
  calcium carbonate
  calcium oxide,
  optionally, but preferably, a radio-opacifier, very preferentially zirconium oxide,
  and optionally pigments, for example iron oxides.

The aqueous phase comprises calcium chloride, preferably calcium chloride dihydrate $CaCl_2.2H_2O$, a water reducing agent, preferably polycarboxylate, namely a base of polymethyl acrylic acid partially esterified by ethylenic polyoxide chains, highly preferentially polyfunctional monomers of methacrylate and acrylate types (e.g., Neomer™ products by Sanyo Chemicals) or modified polycarboxylate ethers (e.g., Glenium® product by BASF Corporation), and water suitable for preparing medicaments. Before dissolution in the aqueous phase, the calcium chloride is in powder form and may also be present in the solid phase.

The solid phase and aqueous phase are mixed in a mass ratio of solid phase to aqueous phase ranging from 2 to 4.5, preferably ranging from 3 to 4. Preferably 700 mg of solid phase are mixed with 170 microlitres of aqueous phase with a density greater than 1, approximately 1.2.

The reaction between the calcium silicate and water occurs on the surface of each calcium silicate crystal. CSH and calcium hydroxide $Ca(OH)_2$ precipitate on the surface of the crystals and between the pores of the crystals. The kernels of the calcium silicate crystals do not react and are progressively surrounded, until they are coated, with CSH relatively impermeable to water, which will progressively reduce the possibilities of subsequent reactions. The hardening of the paste is due to the progressive formation of more and more CSH on the crystals.

According to one embodiment of the invention, the composition is a dental composition intended to be in prolonged contact (more than 30 days) with dental tissues. The composition according to the invention is particularly intended for restoring decay lesions in dental crowns.

The composition according to the invention may be used as an apical or canal filling and apexification material.

The composition according to the invention is also particularly useful for direct or indirect pulp capping, in particular for covering the afflicted part of the pulp, since it maintains the vitality of the dental pulp. In particular it can be used for capping the radicular pulp in pulpotomy operations (ablation of the cameral pulp followed by capping of the radicular pulp). The composition according to the invention is also particularly well suited for repairing and regenerating the damaged dentine-pulp complex.

The composition according to the invention promotes the formation of dentine and thus contributes to the creation of a dentine barrier protecting the pulp.

The composition according to the invention can be used as a dentine substitute.

The composition according to the invention can also be used in endodontic surgery, in particular for retrofilling.

The composition according to the invention can also be used as a filling material, in particular for bone filling, for example in dental or maxilliary surgery.

In some applications, the composition according to the invention is an implant.

The composition according to the invention also has the advantage of being perfectly biocompatible, in conformity with the standard ISO 7405-2008: it is not cytotoxic, it is not sensitising, which means that it does not create oedema or erythema, it is not mutagenic, and it does not cause skin irritation or eye irritation.

The composition according to the invention also induces the formation of new dentine tissue in situ.

EXAMPLES

The composition according to the invention results from the mixing of 170 microlitres of an aqueous phase as below and 700 mg of a solid phase as below, for example using a vibrating mixer of the Linea Tac vibrator type sold by the Italian company Montegrosso d'Asti at 4200 oscillations per minute for 1 to 50 seconds, typically 30 seconds.

The composition is mixed by the practitioner as soon as the mixture is produced. The material does not change during the first six minutes, which corresponds to the working time of the practitioner. The practitioner uses it in order to position the material and model it to his convenience.

Examples of Liquid Phases

| Designation of raw materials | Quantity (g) for 100 g Composition # | | | | | |
|---|---|---|---|---|---|---|
| of liquid phase | a | b | c | d | e | f |
| Calcium chloride dihydrate | 29.4 | 15 | 30.4 | 30.4 | 25.2 | 29.6 |
| Neomer ™ | 2 | 2.5 | 1.5 | | | 1 |
| Glenium ® | | | | 1.5 | 2 | 1 |
| Purified water | 68.6 | 82.5 | 68.1 | 68.1 | 72.8 | 68.4 |

Examples of Solid Phases

| Designation of raw materials | Quantity (mg) for 100 g Composition # | | | | | | | | | |
|---|---|---|---|---|---|---|---|---|---|---|
| of solid phase | 1 | 2 | 3 | 4 | 5 | 6 | 7 | 8 | 9 | 10 |
| Tricalcium silicate | 75 | 79.82 | 80.67 | 76.5 | 75.05 | 87 | 78.7 | 75.7 | 70.7 | 69.5 |
| Zirconium oxide | | 5 | 5 | 5 | 15 | | | 19 | 12 | 24 |
| Bismuth oxide | 5 | | | 5 | | 7.4 | 15 | | 12 | |
| Calcium oxide | 0.35 | 0.15 | 0.25 | 0.1 | 0.3 | 0.5 | 0.2 | 0.3 | 0.3 | 1 |
| Calcium carbonate | 19.6 | 15 | 14 | 13.36 | 9.5 | 5 | 6.05 | 5 | 5 | 5.5 |
| Yellow iron oxide | 0.05 | | 0.07 | 0.04 | | 0.02 | 0.03 | | | |
| Red iron oxide | | 0.03 | 0.01 | | 0.08 | 0.02 | 0.02 | | | |
| Brown iron oxide | | | | | 0.07 | | | | | |

The d50 granulometry of the tricalcium silicate crystals used lies between 3 and 3.5 μm, preferably equal to 3 μm, and that of the calcium carbonate lies between 2 and 4 μm, preferably equal 3 μm.

Examples of Compositions of the Invention at Approximately 5 to 6 Minutes after the End of Mixing.

| | Compositions (solid phase + liquid phase) | | | | | | | | | |
|---|---|---|---|---|---|---|---|---|---|---|
| | 1 + a | | 3 + a | | 5 + a | | 9 + a | | 10 + a | |
| | (mg) | (%) | (mg) | (%) | (mg) | (%) | (mg) | (%) | (mg) | (%) |
| Tricalcium silicate | 511.92 | 56.63 | 551.61 | 61.02 | 512.27 | 56.67 | 481.82 | 53.30 | 473.42 | 52.37 |
| Zirconium oxide | 0 | 0 | 35 | 3.87 | 105 | 11.62 | 84 | 9.29 | 168 | 18.58 |
| Bismuth oxide | 35 | 3.87 | 0 | 0 | 0 | 0 | 84 | 9.29 | 0 | 0 |
| Calcium oxide | 2.45 | 0.27 | 1.75 | 0.19 | 2.1 | 0.23 | 2.1 | 0.23 | 7 | 0.77 |
| Calcium carbonate | 137.2 | 15.18 | 98 | 10.84 | 66.5 | 7.36 | 35 | 3.87 | 38.5 | 4.26 |
| Yellow iron oxide | 0.35 | 0.04 | 0.49 | 0.05 | 0 | 0 | 0 | 0 | 0 | 0 |
| Red iron oxide | 0 | 0 | 0.07 | 0.01 | 0.56 | 0.06 | 0 | 0 | 0 | 0 |
| Brown iron oxide | 0 | 0 | 0 | 0 | 0.49 | 0.05 | 0 | 0 | 0 | 0 |
| CSH | 18.54 | 2.05 | 18.54 | 2.05 | 18.54 | 2.05 | 18.54 | 2.05 | 18.54 | 2.05 |
| Calcium chloride dihydrate | 59.976 | 6.63 | 59.976 | 6.63 | 59.976 | 6.63 | 59.976 | 6.63 | 59.976 | 6.63 |
| Neomer ™ | 4.08 | 0.45 | 4.08 | 0.45 | 4.08 | 0.45 | 4.08 | 0.45 | 4.08 | 0.45 |
| Water | 134.484 | 14.88 | 134.484 | 14.88 | 134.484 | 14.88 | 134.484 | 14.88 | 134.484 | 14.88 |

The compressive strength of the above compositions was tested 24 hours after the mixing of the solid and liquid phases. The results are as follows:

| Composition (solid phase + liquid phase) | 1 + a | 3 + a | 5 + a | 9 + a | 10 + a |
|---|---|---|---|---|---|
| Compressive strength (MPa), 24 h after mixing | / | 250 | 215 | 186 | 245 |

The compositions tested in these examples have a compressive strength greater than 50 MPa when the composition was manufactured more 24 hours earlier.

The compositions tested in these examples have a porosity of less than 10%.

The invention claimed is:

1. A composition comprising:
   from 5% to 65%, by weight with respect to the total weight of the composition, of calcium silicate crystals;
   from 1% to 20%, by weight with respect to the total weight of the composition, of calcium carbonate crystals;
   from more than 0% to 50% by weight with respect to the total weight of the composition, of a compound of general formula mCaO.nSiO2.pH2O in which m and n each independently vary from 1 to 3 and p varies from 3 to 6;
   wherein the ratio between d50 granulometry of the calcium silicate crystals and d50 granulometry of the calcium carbonate crystals is less than 10.

2. The composition of claim 1, comprising from 1% to 40% by weight with respect to the total weight of the composition, of a compound of general formula mCaO.nSiO2.pH2O in which m and n each independently vary from 1 to 3 and p varies from 3 to 6.

3. The composition of claim 1, wherein the calcium silicate is pure tricalcium silicate.

4. The composition of claim 1, wherein the calcium silicate is a mixture of tricalcium silicate and dicalcium silicate, said mixture being such that it contains no more than 10% by weight of dicalcium silicate with respect to the total weight of the calcium silicates present in the composition.

5. The composition of claim 1, further comprising a setting accelerator.

6. The composition of claim 5, wherein the setting accelerator is calcium oxide.

7. The composition of claim 1, further comprising a radiopacifier.

8. The composition of claim 7, wherein the radiopacifier is zirconium oxide or bismuth oxide.

9. The composition of claim 1, further comprising at least one pigment.

10. The composition of claim 9, wherein the pigment is at least one iron oxide.

11. The composition of claim 1, further comprising at least one plasticiser.

12. The composition of claim 1, wherein the compressive strength of said composition is greater than 50 MPa when the composition was manufactured more than one hour ago.

13. The composition of claim 1, wherein the compressive strength of said composition is greater than 50 MPa when the composition was manufactured more than 24 hours ago.

14. The composition of claim 1, wherein the porosity of said composition is less than 10%.

15. A method of preparing the composition of claim 1, the method comprising mixing a solid phase consisting of a mixture of powders and an aqueous phase, said solid phase comprising:
   calcium silicates comprising pure tricalcium silicate or a mixture of tricalcium silicate and dicalcium silicate comprising more than 90% by weight of tricalcium silicate and less than 10% by weight of dicalcium silicate, compared with the total weight of the calcium silicates;
   calcium carbonate; and
   calcium oxide;

wherein the ratio between d50 granulometry of the calcium silicates and d50 granulometry of the calcium carbonate is less than 10;
said aqueous phase comprising:
calcium chloride;
a water-reducing agent based on a polycarboxylate; and water,
in mass ratio of solid phase to aqueous phase ranging from 2 to 4.5.

16. The method of claim 15, wherein the mass ratio of solid phase to aqueous phase ranges from 3 to 4.

17. The method of claim 15, wherein the solid phase further comprises zirconium oxide and/or at least one pigment.

18. A method comprising contacting a composition of claim 1 to a dental tissue to restore a dental crown that has lost substance, for endodontic treatment, and/or in dental surgery.

* * * * *

UNITED STATES PATENT AND TRADEMARK OFFICE
CERTIFICATE OF CORRECTION

PATENT NO.       : 8,974,586 B2                           Page 1 of 1
APPLICATION NO.  : 13/639688
DATED            : March 10, 2015
INVENTOR(S)      : Gilles Richard and Olivier Marie It is certified that error appears in the above-identified patent and that said Letters Patent is hereby corrected as shown below:

On the title page, Item (73) Assignee, line 2:

Delete "Specialties" and replace with --Specialites-- therefor.

Signed and Sealed this
Twenty-fifth Day of August, 2015

Michelle K. Lee
*Director of the United States Patent and Trademark Office*